United States Patent [19]
Tokuyasu et al.

[11] Patent Number: 6,057,144
[45] Date of Patent: May 2, 2000

[54] CHITIN DEACETYLASE GENE, VECTOR CONTAINING SAID GENE AND TRANSFORMANT

[75] Inventors: Ken Tokuyasu; Yutaka Mori; Shioka Hamamatsu, all of Tsukuba; Kiyoshi Hayashi, Tsuchiura, all of Japan

[73] Assignee: Director of National Food Research Institute, Ministry of Agriculture, Forestry and Fisheries, Tsukuba, Japan

[21] Appl. No.: 09/013,067

[22] Filed: Jan. 26, 1998

[30]     Foreign Application Priority Data

Dec. 2, 1997 [JP] Japan .................................... 9-345737

[51] Int. Cl.[7] ............................. C12N 15/55; C12N 9/78; C12N 1/21; C12N 15/63
[52] U.S. Cl. ................. 435/227; 435/252.3; 435/252.33; 435/320.1; 435/254.11; 536/23.2
[58] Field of Search ................................. 435/227, 252.3, 435/252.33, 254.11, 320.1; 536/23.2

[56]     References Cited

U.S. PATENT DOCUMENTS 5,525,502    6/1996    Thireos et al. ........................ 435/240.2

OTHER PUBLICATIONS

I. Tsigos et al., "Purification and Characterization of Chitin Deacetylase from Colletorichum lindemuthianum", J. Biol. Chem. 270(44): 26286–26291, Nov. 1995.

*Primary Examiner*—Rebecca E. Prouty
*Attorney, Agent, or Firm*—Oblon, Spivak, McClelland, Maier & Neustadt, P.C.

[57]     ABSTRACT

A chitin deacetylase gene encoding a protein, a plasmid vector containing said gene and a transformant transformed with the plasmid vector. An object of the present invention is to make contribution to the industrial production of said enzyme, by cloning the gene of said enzyme to elucidate the structure of the gene and express the gene.

7 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 663 base pairs
      (B) TYPE: nucleic acid
      (C) STRANDEDNESS: double
      (D) TOPOLOGY: linear (ii) MOLECULE TYPE: cDNA (vi) ORIGINAL SOURCE:
      (A) ORGANISM: Colletotrichum lindemuthianum
      (B) STRAIN: ATCC 56676

(ix) FEATURE:
      (A) NAME/KEY: CDS
      (B) LOCATION: 1..663
      (D) OTHER INFORMATION: /note= "METHOD OF DETERMINING THE CHARACTERISTICS: E"

(xi) SEQUENCE DESCRIPTION: SEQ ID NO:1:

```
CAG GTT CCC GTG GGC ACA CCC ATC CTC CAG TGC ACC CAG CCT GGT TTG        48
Gln Val Pro Val Gly Thr Pro Ile Leu Gln Cys Thr Gln Pro Gly Leu
  1               5                  10                  15

GTT GCT CTG ACC TAC GAC GAC GGT CCT TTC ACC TTC ACC GCT CAG CTC        96
Val Ala Leu Thr Tyr Asp Asp Gly Pro Phe Thr Phe Thr Ala Gln Leu
                 20                  25                  30

CTC GAC ATC TTG AAG CAG AAC GAC GTC AAG GCG ACC TTC TTC GTC AAC       144
Leu Asp Ile Leu Lys Gln Asn Asp Val Lys Ala Thr Phe Phe Val Asn
             35                  40                  45

GGC AAC AAC TGG GCC AAC ATC GAG GCC GGA TCC AAC CCC GAC ACG ATC       192
Gly Asn Asn Trp Ala Asn Ile Glu Ala Gly Ser Asn Pro Asp Thr Ile
         50                  55                  60

CGC CGC ATG CGC GCC GAC GGC CAC CTC GTC GGC TCT CAC ACG TAC GCT       240
Arg Arg Met Arg Ala Asp Gly His Leu Val Gly Ser His Thr Tyr Ala
 65                  70                  75                  80

CAC CCG GAC CTC AAC ACG CTC TCC TCC GCG GAC CGC ATC TCC CAG ATG       288
His Pro Asp Leu Asn Thr Leu Ser Ser Ala Asp Arg Ile Ser Gln Met
                 85                  90                  95

CGG CAG CTC GAG GAG GCC ACC CGC CGC ATC GAC GGC TTC GCG CCC AAG       336
Arg Gln Leu Glu Glu Ala Thr Arg Arg Ile Asp Gly Phe Ala Pro Lys
                100                 105                 110

TAC ATG CGC GCG CCG TAC CTG TCG TGC GAC GCG GGC TGC CAG GGC GAC       384
Tyr Met Arg Ala Pro Tyr Leu Ser Cys Asp Ala Gly Cys Gln Gly Asp
            115                 120                 125

CTC GGC GGC CTC GGA TAC CAC ATC ATC GAC ACC AAC CTC GAC ACC AAG       432
Leu Gly Gly Leu Gly Tyr His Ile Ile Asp Thr Asn Leu Asp Thr Lys
```

-continued

```
          130                 135                 140
GAC TAC GAG AAC AAC AAG CCC GAG ACC ACC CAC CTC TCG GCC GAG AAG      480
Asp Tyr Glu Asn Asn Lys Pro Glu Thr Thr His Leu Ser Ala Glu Lys
145                     150                 155                 160

TTC GAC AAC GAG CTG AGC GGC GAC GTC GGC GCC AAC AGC TAC ATT GTC      528
Phe Asp Asn Glu Leu Ser Gly Asp Val Gly Ala Asn Ser Tyr Ile Val
                    165                 170                 175

CTC TCG CAC GAC GTC CAC GAG CAG ACG GTC GTC TCC CTC ACG CAG AGG      576
Leu Ser His Asp Val His Glu Gln Thr Val Val Ser Leu Thr Gln Arg
                180                 185                 190

CTG ATT GAC ACG CTC AAG AGC AAG GGC TAC CGC GCC GTC ACC GTC GGC      624
Leu Ile Asp Thr Leu Lys Ser Lys Gly Tyr Arg Ala Val Thr Val Gly
            195                 200                 205

GAG TGC CTC GGC GAC GCC CCG GAG AAC TGG TAC AAG GCG                  663
Glu Cys Leu Gly Asp Ala Pro Glu Asn Trp Tyr Lys Ala
210                 215                 220
```

(2) INFORMATION FOR SEQ ID NO:2:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Colletotrichum lindemuthianum
        (B) STRAIN: ATCC 56676

(ix) FEATURE:
        (A) NAME/KEY: Peptide
        (B) LOCATION: 1..51
        (D) OTHER INFORMATION: /note= "N-TERMINAL FRAGMENT; DIRECT
            ORIGIN: CHITIN DEACETYLASE"

(xi) SEQUENCE DESCRIPTION: SEQ ID NO:2:

```
Gln Val Pro Val Gly Thr Pro Ile Leu Gln Cys Thr Gln Pro Gly Leu
1               5                   10                  15

Val Ala Leu Thr Tyr Asp Asp Gly Pro Phe Thr Phe Thr Ala Gln Leu
            20                  25                  30

Leu Asp Ile Leu Lys Gln Asn Asp Val Lys Ala Thr Phe Val Asn
        35                  40                  45

Gly Asn Asn
    50
```

(2) INFORMATION FOR SEQ ID NO:3:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Colletotrichum lindemuthianum
        (B) STRAIN: ATCC 56676

(ix) FEATURE:
        (A) NAME/KEY: Peptide
        (B) LOCATION: 1..50
        (D) OTHER INFORMATION: /note= "FRAGMENT OF INTERMEDIATE
            PART; DEGRADATION PRODUCTS OF CHITIN DEACETYLASE"

(xi) SEQUENCE DESCRIPTION: SEQ ID NO:3:

```
Ala Thr Phe Phe Val Asn Gly Asn Asn Trp Ala Asn Ile Glu Ala Gly
1               5                   10                  15

Ser Asn Pro Asp Thr Ile Arg Arg Met Arg Ala Asp Gly His Leu Val
            20                  25                  30

Gly Ser His Thr Tyr Ala His Pro Asp Leu Asn Thr Leu Ser Ser Ala
        35                  40                  45

Asp Arg
    50
```

(2) INFORMATION FOR SEQ ID NO:4:

(i) SEQUENCE CHARACTERISTICS:
        (A) LENGTH: 84 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Colletotrichum lindemuthianum
        (B) STRAIN: ATCC 56676

(ix) FEATURE:
        (A) NAME/KEY: Peptide
        (B) LOCATION: 1..84
        (D) OTHER INFORMATION: /note= "FRAGEMNT OF INTERMEDIATE
            PART; DEGRADATION PRODUCTS OF CHITIN DEACETYLASE"

(xi) SEQUENCE DESCRIPTION: SEQ ID NO:4:

```
Tyr Met Arg Ala Pro Tyr Leu Ser Xaa Asp Ala Gly Xaa Gln Gly Asp
1               5                   10                  15

Leu Gly Gly Leu Gly Tyr His Ile Ile Asp Thr Asn Leu Asp Xaa Lys
            20                  25                  30

Asp Tyr Glu Asn Asn Lys Xaa Glu Thr Thr His Leu Ser Ala Glu Lys
        35                  40                  45

Phe Asp Asn Glu Leu Ser Gly Asp Val Gly Ala Asn Ser Tyr Ile Val
    50                  55                  60

Leu Ser His Asp Val His Glu Gln Thr Val Val Ser Leu Thr Gln Arg
65                  70                  75                  80

Leu Ile Asp Thr
```

(2) INFORMATION FOR SEQ ID NO:5:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Colletotrichum lindemuthianum
        (B) STRAIN: ATCC 56676

(ix) FEATURE:
        (A) NAME/KEY: Peptide
        (B) LOCATION: 1..27
        (D) OTHER INFORMATION: /note= "FRAGMENT OF INTERMEDIATE
            PART, DEGRADATION PRODUCTS OF CHITIN DEACETYLASE"

(xi) SEQUENCE DESCRIPTION: SEQ ID NO:5:

```
Leu Ile Asp Thr Xaa Lys Ser Lys Gly Tyr Arg Ala Val Thr Val Gly
1               5                   10                  15
```

Glu Xaa Leu Gly Asp Ala Pro Glu Asn Trp Tyr
        20                  25

(2) INFORMATION FOR SEQ ID NO:6:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR REACTION PRODUCTS"

(vi) ORIGINAL SOURCE:
        (A) ORGANISM: Colletotrichum lindemuthianum
        (B) STRAIN: ATCC 56676

(xi) SEQUENCE DESCRIPTION: SEQ ID NO:6:

```
AACATCGAGG CCGGGTCCAA CCCCGACACG ATCCGCCGCA TGCGCGCCGA CGGCCACCTC    60

GTCGGCTCTC ACACGTACGC TCACCCGGAC CTCAACACGC TCTCCTCCGC GGACCGCATC   120

TCCCAGATGC GGCAGCTCGA GGAGGCCACC CGCCGCATCG ACGGCTTCGC GCCCAAGTAC   180

ATGCGCGCGC CGTACCTGTC GTGCGACGCG GGCTGCCAGG GCGACCTCGG CGGCCTCGGA   240

TACCACATCA TCGACACCAA CCTCGACACC AAGGACTACG AGAACAACAA GCCCGAGACC   300

ACCCACCTCT CGGCCGAGAA GTTCGACAAC GAGCTGAGCG GCGACGTCGG CGCCAACAGC   360

TACATTGTCC TCTCGCACGA CGTCCACGAG CAGACGGTCG TCTCCCTCAC GCAGAGGCTG   420

ATTGACACGC TCAAGAGCAA GGGC                                          444
```

(2) INFORMATION FOR SEQ ID NO:7:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR REACTION PRODUCTS"

(vi) ORIGINAL SOURCE:
        (A) ORGANISM: Colletotrichum lindemuthianum
        (B) STRAIN: ATCC 56676

(xi) SEQUENCE DESCRIPTION: SEQ ID NO:7:

```
GTCGACATGC ACTTCTCGAC CCTTCTTGGC GCCGCGGCTA CTGCTGCTCT CGCTGGCAGC    60

ACGAACGCAA GCCCTCTCGC CCGTCGCCAG GTTCCCGTGG GCACACCCAT CCTCCAGTGC   120

ACCCAGCCTG GTCTGGTTGC TCTGACCTAC GACGACGGTC CTTTCACCTT CACCGCTCAG   180

CTCCTCGACA TCTTGAAGCA GAACGACGTC AAGGCGACCT TCTTCGTCAA CGGCAACAAC   240

TGGGCCAACA TCGAGGCCGG ATCCAACCCC GACACGATCC GCCGCATGCG CGCCGACGGC   300

CACCTCGTCG GCTCTCACAC GTACGCTCAC CCGGACCTCA ACACGCTCTC CTCCGCGGAC   360

CGCATCTCCC AGATGCGGCA GCTCGAGGAG GCCACCCGCC GCATCGACGG CTTCGCGCCC   420

AAGTACATGC GCGCGCCGTA CCTGTCGTGC GACGCGGGCT GCCAGGGCGA CCTCGGCGGC   480

CTCGGATACC ACATCATCGA CACCAACCTC GACACCAAGG ACTACGAGAA CAACAAGCCC   540

GAGACCACCC ACCTCTCGGC CGAGAAGTTC GACAACGAGC TGAGCGGCGA CGTCGGCGCC   600

AACAGCTACA TTGTCCTCTC GCACGACGTC CACGAGCAGA CGGTCGTCTC CCTCACGCAG   660

AGGCTGATTG ACACGCTCAA GAGCAAGGGC TACCGCGCCG TCACCGTCGG CGAGTGCCTC   720
```

-continued

```
GGCGACGCCC CGGAGAACTG GTACAAGGCG AGATCT                                    756
```

(2) INFORMATION FOR SEQ ID NO:8:

(i) SEQUENCE CHARACTERISTICS:
        (A) LENGTH: 221 amino acids
        (B) TYPE: amino acid
        (D) TOPOLOGY: linear (ii) MOLECULE TYPE: protein (xi) SEQUENCE DESCRIPTION: SEQ ID NO:8:

```
Gln Val Pro Val Gly Thr Pro Ile Leu Gln Cys Thr Gln Pro Gly Leu
 1               5                  10                  15

Val Ala Leu Thr Tyr Asp Asp Gly Pro Phe Thr Phe Thr Ala Gln Leu
            20                  25                  30

Leu Asp Ile Leu Lys Gln Asn Asp Val Lys Ala Thr Phe Phe Val Asn
            35                  40                  45

Gly Asn Asn Trp Ala Asn Ile Glu Ala Gly Ser Asn Pro Asp Thr Ile
50                      55                  60

Arg Arg Met Arg Ala Asp Gly His Leu Val Gly Ser His Thr Tyr Ala
65                  70                  75                  80

His Pro Asp Leu Asn Thr Leu Ser Ser Ala Asp Arg Ile Ser Gln Met
            85                  90                  95

Arg Gln Leu Glu Glu Ala Thr Arg Arg Ile Asp Gly Phe Ala Pro Lys
            100                 105                 110

Tyr Met Arg Ala Pro Tyr Leu Ser Cys Asp Ala Gly Cys Gln Gly Asp
            115                 120                 125

Leu Gly Gly Leu Gly Tyr His Ile Ile Asp Thr Asn Leu Asp Thr Lys
130                     135                 140

Asp Tyr Glu Asn Asn Lys Pro Glu Thr Thr His Leu Ser Ala Glu Lys
145                 150                 155                 160

Phe Asp Asn Glu Leu Ser Gly Asp Val Gly Ala Asn Ser Tyr Ile Val
                165                 170                 175

Leu Ser His Asp Val His Glu Gln Thr Val Val Ser Leu Thr Gln Arg
            180                 185                 190

Leu Ile Asp Thr Leu Lys Ser Lys Gly Tyr Arg Ala Val Thr Val Gly
            195                 200                 205

Glu Cys Leu Gly Asp Ala Pro Glu Asn Trp Tyr Lys Ala
210                 215                 220
```

CHITIN DEACETYLASE GENE, VECTOR CONTAINING SAID GENE AND TRANSFORMANT

FIELD OF THE INVENTION

The present invention relates to a chitin deacetylase gene, a plasmid vector containing said gene and a transformant.

Chitin deacetylase (EC 3.5.1.41) is an enzyme hydrolyzing the N-acetyl group in the N-acetylglucosamine residue of chitin, and has an ability of decomposing N-acetylglucosamine residue into glucosamine residue and acetic acid.

Through the deacetylation of chitin, chitosan is prepared as a useful material in the fields of food industry, pharmaceutical industry and the like. Accordingly, said enzyme is useful for designing an effective utilization of chitin which is a waste resource.

Furthermore, said enzyme can be used for preparing chitosan oligosaccharide from chitin oligosaccharide, and for enzymatically deacetylating the N-acetyl groups in other aminosugar residues.

BACKGROUND OF THE INVENTION

As has been described above, chitin deacetylase is an enzyme hydrolyzing the N-acetyl groups in chitin, chitin oligosaccharide, and other compounds containing N-acetylated aminosugar residues.

As described above, the usefulness of chitosan, which is a deacetylated product of chitin, is approved in a wide variety of fields. In the food field alone, the usefulness thereof is illustrated by for example thickening action, cholesterol decreasing action, hypotensive action, prophylactic effect against gout and hyperurinacidemia, prophylactic effect against osteoporosis, promotion of the growth of Bifidus bacteria, suppression of the growth of *E. coli* and *Clostridium perfringens*, antitumor activity and the like.

Conventionally, the N-acetyl group in sugar residues has been hydrolyzed, primarily by chemical hydrolysis with alkalis. It has been remarked that the method is disadvantageous due to the occurrence of side reactions and the difficulty in the control of the reaction and the generation of alkaline liquid waste.

As a means for overcoming the disadvantages, energetic research works have been carried out over an enzymatic deacetylation method under mild conditions, by using chitin deacetylase. Specifically, attention has been focused on a chitin deacetylase derived from Deuteromycotina (imperfect fungi) (Japanese Patent Kokai Hei 8-289785).

The chitin deacetylase derived from an imperfect fungi is advantageous in that the enzymatic reaction is hardly inhibited by a reaction product, acetic acid and in that low molecular chitin oligosaccharides etc. can also be deacetylated. Therefore, the deacetylase is very suitable for industrial use. Furthermore, the enzyme has a wide range of activities such as activity to eliminate the N-acetyl group in the N-acetylated aminosugar residues other than those in chitin, so the enzyme can be applied to the synthesis of novel sugar chains.

The imperfect fungi having been researched most energetically as bacteria to obtain a chitin deacetylase is *Colletotrichum lindemuthianum*.

Because *Colletotrichum lindemuthianum* is a plant pathogenic fungus, however, the handling thereof is so disadvantageously difficult in terms of safety. From the respect of production of the enzyme, additionally, said fungus is disadvantageous in that a longer time is needed for the enzyme to be secreted in a fungal culture broth, but the enzyme to be recovered is a little.

SUMMARY OF THE INVENTION

It is an object of the present invention to overcome the problems described above and to make contribution to the industrial production of a chitin deacetylate derived from imperfect fungi, by cloning a gene of said enzyme to elucidate the structure of the gene and express the gene so as to more effectively utilize the enzyme.

The inventors have made investigations so as to elucidate the structural gene of chitin deacetylase. The inventors have successfully cloned the gene of chitin deacetylase from the microorganism belonging to genus Colletotrichum having an ability of producing said enzyme. As a result, the present invention was completed.

The invention is the chitin deacetylase gene encoding the protein of the amino acid sequence of Sequence No. 1 in Sequence Listing.

The invention is a DNA nucleotide sequence hybridizable to the nucleotide sequence of the gene described above and encoding a protein with the deacetylase activity of the N-acetyl group in N-acetylated aminosugar residues.

The invention is a plasmid vector containing the chitin deacetylase gene described above.

The invention is a transformant produced by transformation via the plasmid vector described above.

DETAILED DESCRIPTION OF THE INVENTION

The inventors have highly purified chitin deacetylase recovered from a culture broth of an imperfect fungi belonging to genus Colletotrichum, having an ability of producing chitin deacetylase, and have determined the N-terminal amino acid sequence thereof. By decomposing the chitin deacetylase with a protease, furthermore, peptide fragments were prepared to determine the amino acid sequences thereof.

Subsequently, the inventors have prepared a primer on the basis of the nucleotide sequence deduced from the amino acid sequences thereof. Through polymerase chain reaction (PCR) using the primer and the genomic DNA extracted from microorganism belonging to the genus Colletotrichum, amplified products were recovered. The PCR products recovered were cloned for the analysis thereof with a DNA sequencer, to determine the DNA sequence.

The DNA sequence was translated into amino acid, which corresponded to the amino acid sequences of the preliminarily recovered peptide fragments. Thus, it was suggested that these peptide fragments were parts of the gene of chitin deacetylase.

On the basis of the determined DNA sequence, then, a primer was again constructed, sufficiently taking account of codon stringency, to clone the chitin deacetylase gene, by using cDNA prepared from RNA by using a reverse transcriptase as a template.

Firstly, PCR was carried out on the basis of the cDNA, by using a primer containing an oligo dT sequence and the primer mentioned above, to analyze the sequence 3' downstream the known gene sequence and determine the DNA nucleotide sequence to the termination codon, whereby the amino acid sequence of the C-terminal region was determined.

Continuously, an adapter sequence was adapted to the upstream of the cDNA by using a commercially available 5'-RACE kit, for PCR by using a primer encoded with a part of the adapter sequence and a primer prepared from a segment of the known gene sequence, to determine the DNA nucleotide sequence 5' upstream the segment of the known gene sequence to the upstream of the initiation codon. As to the region of the structural gene, the corresponding amino acid sequence was determined.

Furthermore, a primer including the initiation codon and a part corresponding to several amino acids at a part deduced as a signal sequence around the initiation codon was prepared, along with a primer including a part corresponding to several amino acids at the C-terminus, and by carring out PCR with a use of these primers, an amplified fragment containing the whole structural gene of chitin deacetylase was recovered. The fragment was ligated to a plasmid vector, which was then transformed into E. coli by routine method, to recover a transformant.

The invention will now be described in detail hereinbelow.

As has been described above, the chitin deacetylase of the present invention is derived from microorganism belonging to the genus Colletotrichum, having an ability of producing chitin deacetylase.

The imperfect fungi belonging to the genus Colletotrichum, having an ability of producing chitin deacetylase, include for example *Colletotrichum lindemuthianum* ATCC56676 etc.

Chitin deacetylase can be recovered from the culture broth of the above microorganism. More specifically, the microorganism can be cultured in a nutrition medium by routine method, to recover the microbial culture broth, which is then purified by purification means such as column chromatography, FPLC, and HPLC, to recover highly purified chitin deacetylase.

Then, the amino acid sequence of the N-terminus of the purified chitin deacetylase is to be determined. For sequencing, use can be made of a protein sequencer of Type HPG 1005A (manufactured by Hewlett Packard, Co.). The amino acid sequence of the N-terminus was determined, as shown as the Sequence No. 2 in the Sequence Listing.

By further enzymatically degrading the chitin deacetylase, peptide fragments were prepared, to determine the amino acid sequences thereof (see Sequence Nos. 3 to 5 in the Sequence Listing).

By determining the nucleotide sequences from the analyzed amino acid sequences and using a primer prepared on the determined sequences, PCR was carried out with a template DNA extracted from the imperfect fungi belonging to the genus Colletotrichum. The resulting bands (PCR products) were cloned, for the analysis thereof by a DNA sequencer of Type ABI PRISM 377 or 310 (manufactured by Perkin Elmer Applied Biosystems, Co.) to determine the DNA nucleotide sequence. The resulting DNA nucleotide sequence is shown as Sequence No. 6 in the Sequence Listing.

The translation of the DNA nucleotide sequence into amino acid indicated the presence of an amino acid sequence corresponding to a part of the preliminarily recovered peptide fragments (see the Sequence Nos. 3 to 5 in the Sequence Listing). Then, it was confirmed that these peptide fragments were parts of the chitin deacetylase gene.

On the basis of the resulting DNA sequence, then, a primer was re-constructed, sufficiently taking account of codon stringency, for the cloning of the chitin deacetylase using cDNA prepared from RNA by using a reverse-transcriptase, as a template.

Firstly, PCR was carried out, based on the cDNA which was prepared from RNA by using a reverse-transcriptase by using another primer including an oligo dT sequence and the above-mentioned primer, to analyze the sequence 3' downstream the known gene sequence and then determine the DNA nucleotide sequence to the termination codon, whereby the amino acid sequence was determined.

Continuously, an adapter sequence was adapted to the upstream of the cDNA by using a commercially available 5'-RACE kit (Marathon cDNA Amplification kit, manufactured by Clone Tech, Co.), and PCR was carried out by using a primer encoded with a part of the adapter sequence and a primer prepared from a segment of the known gene sequence, to determine the DNA nucleotide sequence 5' upstream the segment of the known gene sequence to the upstream of the initiation codon. As to the region deduced as a signal sequence starting from the initiation codon and the region of the structural gene of the mature protein, the corresponding amino acid sequences were determined.

Furthermore, a primer including the initiation codon and a part corresponding to several amino acids at a part deduced as a signal sequence around the initiation codon was prepared, along with a primer including a part corresponding to several amino acids at the C-terminus, and by using these primers for PCR, an amplified fragment containing the whole structural gene of chitin deacetylase was recovered. The fragment contains the DNA sequence corresponding to the amino acid sequence shown in Sequence No. 1 in the Sequence Listing, following the region deduced as a signal sequence starting from the initiation codon. and thus, the fragment contains the whole enzyme gene of the chitin deacetylase described above.

The chitin deacetylase gene of the present invention contains the nucleotide sequence described in the Sequence No. 1 in the Sequence Listing or has a function substantially the same as that of the sequence. Herein, the term "function substantially the same" means that a gene encoding the same amino acid residue is regarded as substantially the same, based on the codon stringency, even if the sequence thereof is wholly different from that of the gene described as the Sequence No. 1.

The present invention comprises a nucleotide sequence hybridizable to the nucleotide sequence of the gene described above and is coding for a protein having a deacetylase activity of the N-acetyl group in N-acetylated aminosugar residues.

When the overall homology is at about 85% or more, a gene almost homologous to the present invention gene described above can readily be cloned, with reference to the sequence of said Sequence No. 1, by using known genetic engineering manipulation techniques such as DNA hybridization and gene amplification.

The present invention includes a plasmid vector containing said gene; and the present invention includes a transformant produced by transformation with said plasmid vector. More specifically, a DNA fragment containing the nucleotide sequence of the gene described above can be ligated into a plasmid vector such as plasmid vector pCR2.1 (manufactured by In Vitro Gen Co.), thereby transforming the vector into E. coli accoording to the routine method.

The E. coli transformed by using the plasmid vector pCR2.1 (manufactured by In Vitro Gen, Co.) has been deposited as the accession No. of FERM BP-6191 at National Institute of Bioscience and Human-Technology, Agency of Industrial Science and Technology (1-3, Higashi 1-chome, Tsukuba-shi, Ibaraki-ken, Japan).

As is apparent to a person with ordinary skill in the art, furthermore, the chitin deacetylase can be expressed at a large scale in host cells of procaryotic or eucaryotic organisms, by using the DNA sequence according to the present invention. In other words, the enzyme can be expressed by the following routine method.

For example, the gene of the present invention is inserted into an expression vector of a procaryotic or an eucaryotic organism, together with an appropriate modification signal, and the vector is then used for cell transformation. As the modification signal and the expression vector, a wide variety of such signals and vectors have been developed and commercially available, and therefore, use is made of well known ones to a person skilled in the art.

A series of manipulations by using vectors and the method for transformation have already been common, which can be carried out by a person skilled in the art. For example, the method described in J. Sambrook, E. F. Fritsch, T. Maniatis (ed.), "Molecular Cloning; A Laboratory Manual, 2nd edition", Cold Spring Harbor Laboratory Press, (1989) and the like, may be used to carry out the procedures described above.

In accordance with the present invention, the enzyme recovered through the expression of the chitin deacetylase gene promotes the deacetylation reaction of chitin, chitin oligosaccharide, and the N-acetyl groups in other N-acetylated aminosugar residues to efficiently prepare chitosan, chitosan oligosaccharide or other N-deacetylated sugars as useful raw materials in the fields of food processing and pharmaceutical industries.

Conventionally, the recovery of chitin deacetylase from plant pathogenic fungi such as microorganism belonging to the genus Colletotrichum has involved safety and management problems because of the handling of such pathogenic bacteria, and the culture of the microorganism requires a longer period of time. Additionally, the yield of the enzyme has not been satisfactory.

By expressing the chitin deacetylase gene in an appropriate procaryotic or eucaryotic organism by using the plasmid containing the chitin deacetylase gene of the present invention, said enzyme can be procured at a large scale in a safe and speedy manner, with no concern about the problems described above.

In accordance with the present invention, therefore, raw material production industries will further be promoted and facilitated by using chitin deacetylase.

EXAMPLES

The present invention will now be described in examples, but the invention is not limited to these examples.

Example 1

An imperfect fungi Colletotrichum lindemuthianum ATCC 56676 sub-cultured in a slant medium was inoculated in a liquid culture medium, for 18-day culture in darkness at 22° C. By filtering off the microorganism, the microbial culture broth was recovered, which was then purified by using ammonium sulfate precipitation, hydrophobic chromatography, ion exchange chromatography, gel filtration chromatography and the like, to recover a highly purified chitin deacetylase.

The amino acid sequence of the N-terminus of the purified chitin deacetylase was then determined. For such sequencing, a protein sequencer of Type HPG 1005A (manufactured by Hewlett Packard, Co.) was used. The determined amino acid sequence of the N-terminus is shown as the Sequence No. 2 of the Sequence Listing.

When an enzymatic protein was purified by reverse chromatography by using a solvent containing trifluoroacetic acid, the N-terminal part was pyroglutaminated. Therefore, the sequence could never be read. By sequencing after the action with pyroglutamate aminopeptidase (manufactured by Boehringer Mannheim, Co.), however, the peptide sequence starting from the second residue from the N-terminus could be analyzed and determined sequentially.

By limiting degradation of the chitin deacetylase with endoproteinase Lys-C (Boehringer Mannheim, Co.) and endoproteinase Arg-C (Boehringer Mannheim, Co.) to prepare peptide fragments, and then the amino acid sequences thereof were determined (see Sequence Nos. 3 to 5 in the Sequence Listing).

From the determined amino acid sequence, regions with less codon stringency were selected, and by using a primer produced on the basis of the regions, PCR was carried out using DNA extracted from the imperfect fungi belonging to the genus Colletotrichum as a template. The resulting bands (PCR products) were cloned, for the analysis thereof by a DNA sequencer of Type ABI PRISM 377 (manufactured by Perkin Elmer Applied Biosystems, Co.) to determine the DNA nucleotide sequence. The resulting 444 bp nucleotide sequence as sequenced is shown as Sequence No. 6 in the Sequence Listing.

The DNA nucleotide sequence was translated into amino acid, and an amino acid sequence corresponding to a part of the preliminarily recovered peptide fragments (see the Sequence Nos. 3 to 5 in the Sequence Listing) was observed. Then, it was confirmed that these peptide fragments were parts of the chitin deacetylase gene.

On the basis of the resulting DNA sequence, then, a primer was re-constructed, sufficiently taking account of codon stringency, and the cloning of the chitin deacetylase was carried out using cDNA, as a template, which was prepared from RNA by using a reverse-transcriptase (RNA PCR kit (AMV) Ver.2.1, manufactured by Takara Brewery Co.).

Firstly, on the basis of the cDNA prepared through the reaction of a primer containing an oligo dT sequence with RNA as the template by using a reverse transcriptase, PCR was carried out by using both a primer containing an oligo dT sequence and the afore-mentioned primer, to analyze the sequence 3' downstream the known gene sequence and determine the DNA nucleotide sequence to the termination codon, whereby the amino acid sequence was determined.

Continuously, an adapter sequence was adapted to the upstream of the cDNA by using a 5'-RACE kit (Marathon cDNA Amplification kit, manufactured by Clone Tech, Co.), and PCR was carried out by using both a primer encoded with a part of the adapter sequence and a primer prepared from a segment of the known gene sequence, to determine the DNA nucleotide sequence 5' upstream the segment of the known gene sequence to the upstream of the initiation codon, by using a DNA sequencer ABI PRISM 310 (manufactured by Perkin Elmer Applied BioSystems, Co.). As to the region of the structural gene, the corresponding amino acid sequence was determined.

Furthermore, a primer containing the initiation codon and a part corresponding to several amino acids at a part deduced as a signal sequence around the initiation codon was prepared, along with a primer including a part corresponding to several amino acids at the C-terminus, and by using these primers for PCR, an amplified fragment containing the whole structural gene of chitin deacetylase was recovered.

The fragment was ligated into a plasmid vector PCR 2.1 (In Vitro Gen Co.), which was then transformed into *E. coli*, by routine method. The resulting product was inoculated on an LB agar medium containing ampicillin (50 μg/ml) and methicillin (80 μg/ml), for overnight culture at 37° C., to select the transformant (FERM BP-6191) and recover the introduced plasmid, to determine the nucleotide sequence of said enzyme gene (see Sequence No. 7 in the Sequence Listing).

Consequently, the inserted fragment contained the nucleotide sequence shown as Sequence No. 1 in the Sequence Listing, following a sequence deduced as an initiation signal starting from the initiation codon, and it was apparently demonstrated that the fragment contained the whole enzyme gene of the deacetylase according to claim 1.

The entire disclosure of Japanese Patent Application No. 9-345737 filed on Dec. 2, 1997 including specification, claims and summary are incorporated herein by reference in its entirety.

What is claimed is:

1. An isolated nucleic acid encoding a chitin deacetylase having the amino acid sequence of SEQ ID NO: 8.

2. The nucleic acid of claim 1, wherein the chitin deacetylase having the amino acid sequence of SEQ ID NO: 8 is encoded by the DNA sequence of SEQ ID NO: 1.

3. A plasmid vector containing the nucleic acid of claim 1.

4. A cell transformed with the plasmid vector of claim 3.

5. The transformed cell of claim 4, which is *E. Coli* (FERM BP-6191).

6. A method of producing chitin deacetylase, comprising culturing the transformed cell of claim 5 in a culture medium and isolating the chitin deacetylase.

7. The transformed cell of claim 4, which is *E. coli*.

* * * * *